(12) United States Patent
Jau et al.

(10) Patent No.: US 9,448,053 B2
(45) Date of Patent: Sep. 20, 2016

(54) MICROWAVE MOTION SENSOR

(71) Applicant: INDUSTRIAL TECHNOLOGY RESEARCH INSTITUTE, Hsinchu (TW)

(72) Inventors: Je-Kuan Jau, Tainan (TW); Ping-Hsun Wu, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 567 days.

(21) Appl. No.: 13/866,115

(22) Filed: Apr. 19, 2013

(65) Prior Publication Data

US 2013/0234729 A1 Sep. 12, 2013

Related U.S. Application Data

(63) Continuation-in-part of application No. 13/484,732, filed on May 31, 2012, now Pat. No. 8,665,098, which is a continuation-in-part of application No. 12/886,522, filed on Sep. 20, 2010, now Pat. No. 8,698,636.

(30) Foreign Application Priority Data

Nov. 1, 2011 (TW) .............................. 100139869 A
Oct. 17, 2012 (TW) .............................. 101138273 A

(51) Int. Cl.
*G01B 7/14* (2006.01)
*G01S 13/58* (2006.01)
(Continued)

(52) U.S. Cl.
CPC ............... *G01B 7/14* (2013.01); *G01S 13/583* (2013.01); *G01S 13/88* (2013.01); *G08B 13/2491* (2013.01); *A61B 5/05* (2013.01); *A61B 5/11* (2013.01)

(58) Field of Classification Search
CPC ......... G01B 7/14; G01B 7/003; G01S 13/88; G01S 13/583; G08B 13/2491; A61B 5/05; A61B 5/0507; A61B 5/11

USPC .......................................................... 324/642
See application file for complete search history.

(56) References Cited

U.S. PATENT DOCUMENTS 3,221,260 A 11/1965 Henrion
3,479,607 A 11/1969 Ruthroff
(Continued)

FOREIGN PATENT DOCUMENTS

CA 2300463 C 2/2009
CN 1646935 A 7/2005
(Continued)

OTHER PUBLICATIONS

Wang, et al.: "Mutual injection-locked SIL sensor array for vital sign detection with random body movement cancellation." Microwave Symposium Digest (MTT), 2011 IEEE MTT-S International. IEEE, Jun. 10, 2011.
(Continued)

*Primary Examiner* — Jermele M Hollington
*Assistant Examiner* — Robert P Alejnikov, Jr.
(74) *Attorney, Agent, or Firm* — McClure, Qualey & Rodack, LLP

(57) ABSTRACT

A microwave motion sensor including a transmitting device, a signal processing device, a signal processing device, and a path switching device is disclosed. The transmitting device transmits a microwave signal to a space under detection. The receiving device receives a reflected microwave signal reflected from the space under detection. The signal processing device processes the reflected microwave signal received by the receiving device to judge whether there is a disturbance in the space under detection, wherein the signal processing device generates the microwave signal. The path switching device is coupled to the signal processing device and the transmitting device and results in different phase shifts to a plurality of transmission paths travelled by the microwave signal.

14 Claims, 3 Drawing Sheets

(51) Int. Cl.
*G01S 13/88* (2006.01)
*G08B 13/24* (2006.01)
*A61B 5/05* (2006.01)
*A61B 5/11* (2006.01)

(56) References Cited

U.S. PATENT DOCUMENTS

| | | | |
|---|---|---|---|
| 3,670,327 A | 6/1972 | Marsh | |
| 4,109,247 A | 8/1978 | Kaplan | |
| 4,123,755 A | 10/1978 | Fishbein et al. | |
| 4,176,351 A | 11/1979 | DeVita et al. | |
| 4,254,483 A * | 3/1981 | Vidovic | G08B 13/1627 340/507 |
| 4,427,982 A | 1/1984 | Caprio | |
| 4,517,982 A | 5/1985 | Shiga et al. | |
| 4,520,362 A * | 5/1985 | Charlot | H01Q 25/001 342/361 |
| 4,600,890 A | 7/1986 | Horvat | |
| 4,646,754 A | 3/1987 | Seale | |
| 4,953,010 A | 8/1990 | Cowley | |
| 4,958,638 A | 9/1990 | Sharpe et al. | |
| 4,991,585 A | 2/1991 | Mawhinney | |
| 5,458,124 A | 10/1995 | Stanko et al. | |
| 5,650,749 A | 7/1997 | Main | |
| 6,133,802 A | 10/2000 | Ma | |
| 6,369,647 B1 | 4/2002 | Main et al. | |
| 6,369,659 B1 | 4/2002 | Delzer | |
| 6,396,358 B1 * | 5/2002 | Poss | H03K 3/0315 331/177 R |
| 6,587,072 B1 | 7/2003 | Gresham et al. | |
| 6,650,276 B2 * | 11/2003 | Lawless | G01S 7/35 342/159 |
| 7,079,029 B2 * | 7/2006 | Tsuji | G01S 13/38 340/552 |
| 7,103,132 B1 | 9/2006 | Baba | |
| 7,538,718 B2 | 5/2009 | Ikeda et al. | |
| 7,616,148 B2 | 11/2009 | Wu et al. | |
| 7,740,588 B1 | 6/2010 | Sciarra | |
| 8,147,409 B2 | 4/2012 | Shifrin | |
| 2004/0150548 A1 | 8/2004 | Walmsley | |
| 2006/0040739 A1 | 2/2006 | Wells | |
| 2006/0055585 A1 * | 3/2006 | Nagasaku | G01S 13/347 342/28 |
| 2007/0241864 A1 | 10/2007 | Nagai | |
| 2008/0077015 A1 | 3/2008 | Boric-Lubecke et al. | |
| 2008/0079636 A1 | 4/2008 | Mohamadi | |
| 2008/0119716 A1 | 5/2008 | Boric-Lubecke et al. | |
| 2008/0146944 A1 | 6/2008 | Tao et al. | |
| 2008/0183053 A1 | 7/2008 | Borgos et al. | |
| 2009/0240133 A1 * | 9/2009 | Friedman | A61B 5/02028 600/407 |
| 2009/0278728 A1 | 11/2009 | Morgan et al. | |
| 2010/0152600 A1 * | 6/2010 | Droitcour | A61B 5/05 600/534 |
| 2010/0198083 A1 | 8/2010 | Lin et al. | |
| 2010/0240999 A1 | 9/2010 | Droitcour et al. | |
| 2010/0249630 A1 | 9/2010 | Droitcour et al. | |
| 2010/0259305 A1 | 10/2010 | Lee et al. | |
| 2012/0001791 A1 | 1/2012 | Wintermantel | |

FOREIGN PATENT DOCUMENTS

| | | |
|---|---|---|
| CN | 102331290 A | 7/2005 |
| CN | 1800876 | 7/2006 |
| CN | 101006915 | 8/2007 |
| CN | 101093995 | 12/2007 |
| CN | 102356332 A | 2/2012 |
| CN | 102247146 A | 11/2015 |
| DE | 102006008513 A1 | 9/2007 |
| EP | 2180593 A1 | 4/2010 |
| JP | H03142396 A | 6/1991 |
| TW | 373153 | 7/2006 |
| TW | 200901940 A | 1/2009 |
| TW | 201120790 | 6/2011 |
| TW | I347108 | 8/2011 |

OTHER PUBLICATIONS

TW Office Action dated Aug. 1, 2014.
TW Office Action dated Aug. 8, 2014.
English Abstract translation of DE102006008513 (Published Sep. 6, 2007).
Non-Final Office Action issued for U.S. Appl. No. 13/456,849, filed Apr. 26, 2012, mailed Oct. 17, 2013.
TW Office Action dated Dec. 16, 2013.
English language translation of abstract of CN 101006915 (published Aug. 1, 2007).
English language translation of abstract of CN 101093995 (published Dec. 26, 2007).
English language translation of abstract of TW 201120790 (published Jun. 16, 2011).
English language translation of abstract of TW I347108 (published Aug. 11, 2011).
Fletcher, R., et al.; "Low-Cost Differential Front-End for Doppler Radar Vital Sign Monitoring;" IEEE; 2009; pp. 1325-1328.
Main, E., et al.; "FM Demodulation Using an Injection-Locked Oscillator;" IEEE; 2000; pp. 135-138.
Biswas, B.N., et al.; "A Doubly Tracking Discriminator;" IEEE; 2009; pp. 1-4.
Tarar, M., et al.; "Injection-Locked Phase-Locked Loop for BPSK Coherent Demodulation: Theory and Design;" IEEE 2007; pp. 387-390.
Chattopadhyay, T., et al.; "A New Microwave Discriminator;" IEEE; 2003; pp. 1078-1081.
Chattopadhyay, T.P., et al.; "Improved X-Band FM Discriminator;" IEEE Transactions on Microwave Theory and Techniques; vol. MTT-34; No. 4; Apr. 1986; pp. 442-446.
Park, et al: "Arctangent Demodulation With DC Offset Compensation in Quadrature Doppler Radar Receiver Systems"; IEEE Transactions on Microwave Theory and Techniques, vol. 55, No. 5, May 2007.
Xiao, et al.: "Frequency-Tuning Technique for Remote Detection of Heartbeat and Respiration Using Low-Power Double-Sideband Transmission in the K a-Band"; IEEE Transactions on Microwave Theory and Techniques, vol. 54, No. 5, May 2006.
Pan, et al.: "Null point elimination using RF phase shifter in continuous-wave Doppler radar system"; Electronics Letters Oct. 13, 2011 vol. 47 No. 21.
Droitcour, et al.: "Range Correlation and I/ Q Performance Benefits in Single-Chip Silicon Doppler Radars for Noncontact Cardiopulmonary Monitoring"; IEEE Transactions on Microwave Theory and Techniques, vol. 52, No. 3, Mar. 2004.
Girbau, et al.: "Remote Sensing of Vital Signs Using a Doppler Radar and Diversity to Overcome Null Detection"; IEEE Sensors Journal, vol. 12, No. 3, Mar. 2012.
Wang, et al.: "A Novel Vital-Sign Sensor Based on a Self-Injection-Locked Oscillator"; IEEE Transactions on Microwave Theory and Techniques, vol. 58, No. 12, Dec. 2010.
Chin, et al.: "A Fast Clutter Cancellation Method in Quadrature Doppler Radar for Non contact Vital Signal Detection"; 978-1-4244-7732-6/10/$26.00 © 2010 IEEE.
Chuang, et al.: "60-GHz Millimeter-Wave Life Detection System (MLDS) for Noncontact Human Vital-Signal Monitoring"; IEEE Sensors Journal, vol. 12, No. 3, Mar. 2012.
Non-Final Office Action for U.S. Appl. No. 13/484,732 issued by the USPTO on Jun. 6, 2013.
CN Office Action dated Aug. 5, 2015 in corresponding Chinese application (No. 201210488286.3).

* cited by examiner

MICROWAVE MOTION SENSOR

This is a continuation-in-part application of U.S. application Ser. No. 13/484,732, filed May 31, 2012, which is a continuation-in-part Application of application Ser. No. 12/886,522, filed Sep. 20, 2010, which claims the benefit of Taiwan application Serial No. 100139869, filed Nov. 1, 2011. This application claims the benefit of Taiwan application Serial No. 101138273, filed Oct. 17, 2012. The disclosure of which is incorporated by reference herein in its entirety.

TECHNICAL FIELD

The disclosure relates in general to a microwave motion sensor.

BACKGROUND

Motion sensor is normally used in security surveillance or on-site identification. In general, the motion sensor is realized by infrared technology. However, the infrared technology is susceptible to environmental temperature and may even result in detection error or failure.

Based on the Doppler principle, the microwave motion sensor compares the phase shift between the transmitted signal and the received signal. If phase shift occurs, this indicates that there is disturbance source in the environment.

Conventional microwave motion sensor has the advantage of simple architecture but needs to resolve the problem arising from sensing zero points. Referring to FIG. 1, a curve chart showing sensitivity of a conventional microwave motion sensor is shown. As indicated in FIG. 1, the horizontal axis denotes distance and the vertical axis denotes sensing sensitivity. When the signal transmitted from the sensor 100 hits the object under detection 110, the transmitted signal will be reflected as a reception signal. FIG. 1 shows that the radar cannot detect motion at sensing zero points (that is, the sensing sensitivity is zero). That is, when the object under detection 110 is located at sensing zero points, the sensor 100 cannot sense the object under detection 110. The phenomenon of sensing zero points is a common problem to the single-frequency Doppler architecture. The sensing zero points periodically occur at an interval of one quarter wavelength of an electromagnetic wave. Points with largest sensing sensitivity are best sensing points.

Moreover, the microwave motion sensor performs detection with continuous wave radar that transmits and receives signals simultaneously. For Doppler shift detection, a mixer is used to down-convert the carrier frequency, hence resulting in DC offset due to co-frequency reflected wave from environmental clutters. As a result, the receiver is saturated by strong DC signals and thus system sensitivity is considerably reduced.

SUMMARY

According to one exemplary embodiment, a microwave motion sensor including a transmitting device, a signal processing device, a signal processing device, and a path switching device is disclosed. The transmitting device transmits a microwave signal to a space under detection. The receiving device receives a reflected microwave signal reflected from the space under detection. The signal processing device processes the reflected microwave signal received by the receiving device to judge whether there is a disturbance in the space under detection, wherein the signal processing device generates the microwave signal. The path switching device is coupled to the signal processing device and the transmitting device and results in different phase shifts to a plurality of transmission paths which the microwave signal passes through.

According to another exemplary embodiment, a microwave motion sensor including a transmitting device, a receiving device, a path switching device and a signal processing device is disclosed. The transmitting device transmits a microwave signal to a space under detection. The receiving device receives a reflected microwave signal reflected from the space under detection. The path switching device is coupled to the receiving device and results in different phase shifts to a plurality of reception paths which the reflected microwave signal passes through. The signal processing device processes the reflected microwave signal received by the receiving device to judge whether there is a disturbance in the space under detection, wherein the signal processing device generates the microwave signal.

According to an alternative exemplary embodiment, a microwave motion sensor including a transceiving device, a signal processing device, and a path switching device is disclosed. The transceiving device transmits a microwave signal to a space under detection and receives a reflected microwave signal reflected from the space under detection. The signal processing device processes the reflected microwave signal received by the transceiving device to judge whether there is a disturbance in the space under detection, wherein the signal processing device generates the microwave signal. The path switching device is coupled to the signal processing device and the transceiving device and results in different phase shifts to a plurality of paths which the microwave signal and the reflected microwave signal pass through.

The above and other disclosures of the application will become better understood with regard to the following detailed description of the preferred but non-limiting embodiment(s). The following description is made with reference to the accompanying drawings.

Figure 1:
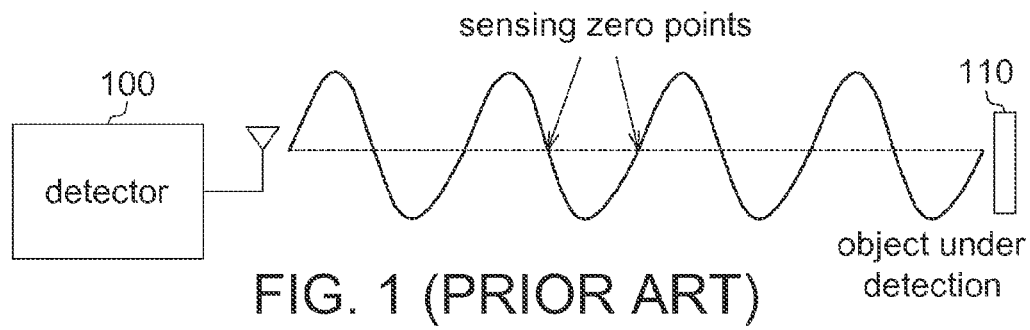
FIG. 1 (PRIOR ART) is a curve chart showing sensitivity of a conventional microwave motion sensor.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

A microwave motion sensor architecture using Doppler principle is disclosed in an embodiment of the disclosure. In an embodiment of the disclosure, output phase or frequency of the oscillator varies when the self-injection-locked voltage-controlled oscillator with high sensitivity receives a Doppler phase modulation signal reflected from an object under detection. By locking the output frequency of the injection-locked voltage-controlled oscillator with a phase-locked loop, external disturbance information is reflected on the control voltage of the injection-locked voltage-controlled oscillator, such that both bandwidth requirement and electromagnetic interference could be reduced.

In an embodiment of the disclosure, the transmission/reception paths with different phase shifts are switched, such that the sensing zero points in the transmission/reception paths do not overlap (the sensing zero points in the transmission/reception paths are even interlaced), and the phenomenon of sensing zero points in single-frequency Doppler radar are eliminated. The sensing sensitivities of these transmission/reception paths are complementary to each other. That is, if a point on one of the paths is at a sensing zero point, then the same point on the other paths will not be a sensing zero point, and the disturbance of the object under detection could thus be stably sensed.

In an embodiment of the disclosure, in detecting low frequency motion/disturbance signals, the transmission signal paths are closed at non-sampling points, so as to reduce the average microwave transmission power.

In an embodiment of the disclosure, a dual-control voltage-controlled oscillator is utilized to adjust the DC level and to eliminate the DC offset, because adding another voltage control port and another varactor changes the resonant frequency of the oscillator resonant cavity, so that the DC level of the output signal of the phase- and self-injection-locked dual-control voltage-controlled oscillator is adjusted to the original predetermined value.

Figure 2:
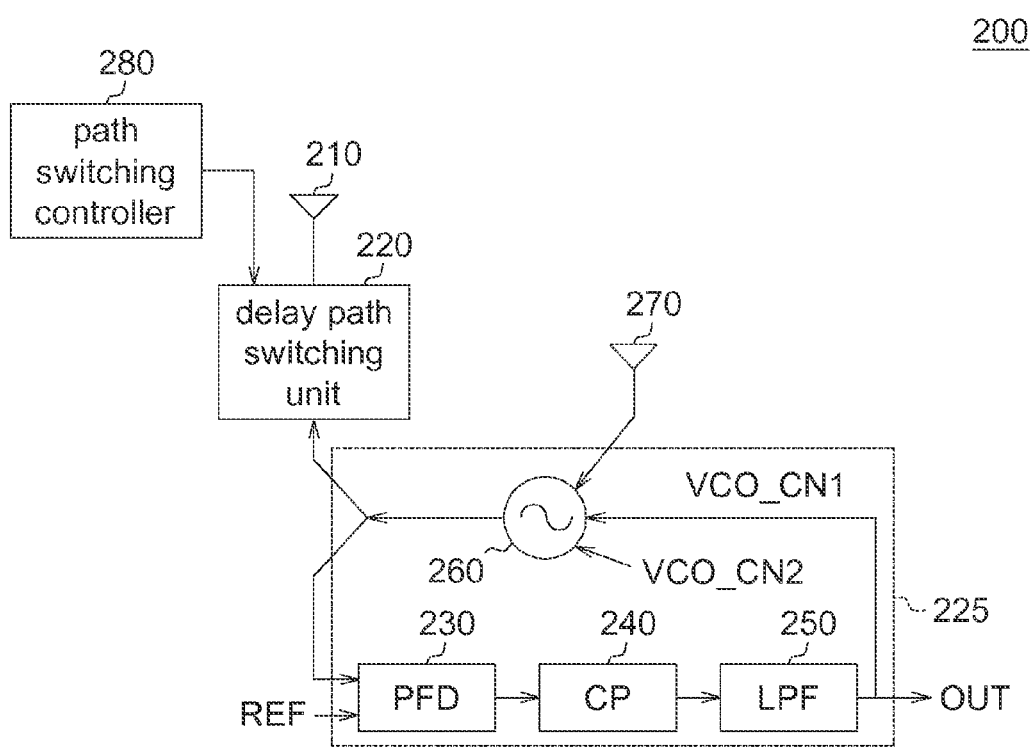
FIG. 2 shows a functional block diagram of a microwave motion sensor according to an embodiment of the disclosure.

FIG. 2 shows a functional block diagram of a microwave motion sensor according to an embodiment of the disclosure. As indicated in FIG. 2, the microwave motion sensor 200 includes at least one transmitting antenna 210, a delay path switching unit 220, a phase-locked loop 225 and at least one receiving antenna 270. The phase-locked loop 225 includes a phase frequency detector (PFD) 230, a charge pump (CP) 240, a low pass filter (LPF) 250 and a dual-control voltage-controlled oscillator 260. In the present embodiment of the disclosure, the phase-locked loop is also referred as a signal processing device. The microwave motion sensor 200 may selectively include a path switching controller 280.

The transmitting antenna 210 transmits a microwave signal, and the receiving antenna 270 receives the reflected microwave signal reflected from the object under detection.

The delay path switching unit 220 switches different delay paths and results in different phase shifts to multiple paths (that is, there are phase shifts existing between multiple paths). Thus, different delay paths can be selected as signal transmission paths. Here below, the switching between two different delay paths is used as an exemplification, but the present disclosure is not limited thereto. In the present disclosure, multiple delay paths can be formed, and the switching can occur between the multiple delay paths.

Figure 3A:
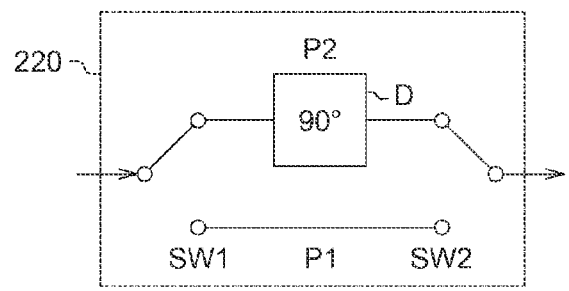
FIG. 3A shows an exemplary example of a delay path switching unit according to an embodiment of the disclosure.

Referring to FIG. 3A, an exemplary example of a delay path switching unit 220 according to an embodiment of the disclosure is shown. As indicated in FIG. 3A, the delay path switching unit 220 includes a delay unit D, and switches SW1 and SW2. The switches SW1 and SW2 may be realized by a single-pole double-throw (SPDT) switch. The delay unit D delays the signal phase by for example but not limited to 90 degrees. That is, the phase shift between the paths P1 and P2 is 90 degrees.

Figure 3B:
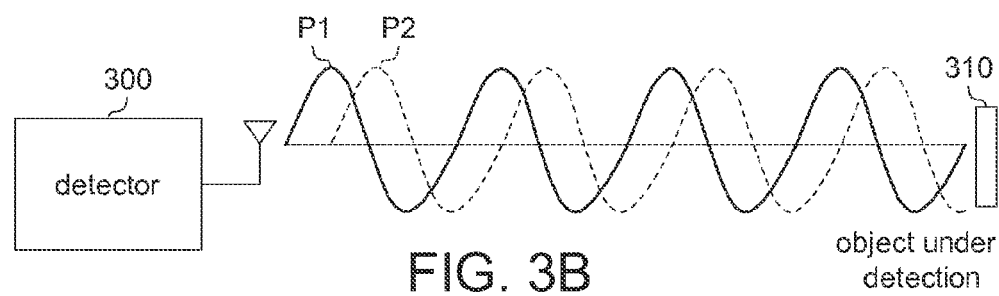
FIG. 3B is a curve chart showing sensitivity according to an embodiment of the disclosure.

Referring to FIG. 3B, a curve chart showing sensitivity change according to an embodiment of the disclosure is shown. In the curve chart, the horizontal axis denotes distance, and the vertical axis denotes sensing sensitivity. FIG. 3B shows that there are two different delay paths whose sensing zero points are different from each other. In the prior art, the sensing zero points incapacitate the sensor of sensing the object under detection. However, the failure of sensing the object under detection is resolved in the embodiment of the disclosure. To put it in greater details, if the object under detection 310 is located at a sensing zero point in one of the paths of the sensor 300, the object under detection 310 will not be located at the sensing zero point on another path.

Referring to FIG. 2. The phase-locked loop 225 controls the dual-control voltage-controlled oscillator 260. The phase-locked loop 225 is also referred as a signal processing device. Details of the phase-locked loop 225 are disclosed below. The phase frequency detector 230 detects an output phase shift (or frequency shift) between an output signal of the dual-control voltage-controlled oscillator 260 and a reference signal REF.

The charge pump 240 outputs a voltage signal according to the detection results of the phase frequency detector 230. The output voltage signal of the charge pump 240 is filtered by the low pass filter 250 as a first control voltage VCO_CN1. The first control voltage VCO_CN1 controls the frequency of the output signal of the dual-control voltage-controlled oscillator 260.

The dual-control voltage-controlled oscillator 260 is realized by an injection-locked voltage-controlled oscillator architecture. The dual-control voltage-controlled oscillator 260 may output and receive a signal at the same time. In other possible embodiments, the output signal of the dual-control voltage-controlled oscillator 260 may be connected to an input end of the delay path switching unit 220 and an input end of the phase-locked loop 225 via a power distributor (not illustrated). After the microwave signal generated from the dual-control voltage-controlled oscillator 260 passes through the delay path switching unit 220, the output microwave signal is transmitted to the object under detection and/or space under detection by the transmitting antenna 210.

If there are disturbance signals existing in the space under detection (disturbance is such as heart beat, breath, or window vibration), when the transmission signal is reflected, the phase or frequency of the reflected signal will change (relative to the transmission signal) due to the Doppler effect. After the reflected signal is received by the receiving antenna 270, the reflected signal can be amplified (the amplifier not illustrated) and injected to the dual-control voltage-controlled oscillator 260. Due to the influence of the reflected signal, the phase or frequency of the output signal of the dual-control voltage-controlled oscillator 260 will change. After the phase variation or frequency variation of the output signal of the dual-control voltage-controlled oscillator 260 is detected by the phase-locked loop 225, the phase-locked loop 225 generates a corresponding first control voltage VCO_CN1 in response to the phase variation or frequency variation, so as to adjust the output frequency of the dual-control voltage-controlled oscillator 260 to the reference frequency. The external disturbance information can be obtained from the observation of the first control voltage VCO_CN1.

In an embodiment of the disclosure, the second control voltage VCO_CN2 of the dual-control voltage-controlled oscillator 260 may eliminate the DC offset. The oscillation frequency of the dual-control voltage-controlled oscillator 260 is determined by the two control voltages VCO_CN1 and VCO_CN2. If the dual-control voltage-controlled oscillator 260 is affected by an external disturbance signal and a DC offset occurs in the primary first control voltage VCO_CN1, variation in the second control voltage VCO_CN2 which is used to eliminate the DC offset of the first control voltage VCO_CN1 is obtained according to equation (1), wherein Kv1, Kv2 are system constants that are determined by the designer.

$$Kv1*\Delta VCO\_CN1 + Kv2*\Delta VCO\_CN2 = 0 \quad (1)$$

Wherein, $\Delta VCO\_CN1$ and $\Delta VCO\_CN2$ respectively denote the variation in the first control voltage VCO_CN1 and the second control voltage VCO_CN2.

Equation (2) is from equation (1) and expressed as:

$$\Delta VCO\_CN2 = -\frac{K_{V1}\Delta VCO\_CN1}{K_{V2}} \quad (2)$$

When it is detected that the DC average value of the primary first control voltage VCO_CN1 varies, the required variation in the second control voltage VCO_CN2 can be obtained from the above equations (1) and (2). Exemplarily but not restrictively, the constant Kv1 is equal to 2 MHz/V and the constant Kv2 is equal to 20 MHz/V. When the system detects that DC average variation of the primary first control voltage VCO_CN1 is 1V, the variation in the second control voltage VCO_CN2 is −0.1V, as from the above equations (1) and (2). That is, the DC offset of the first control voltage VCO_CN1 can be eliminated by stepping down the second control voltage VCO_CN2 by 0.1V. That is, the DC offset of the external disturbance information denoted by the first control voltage VCO_CN1 has been eliminated.

In practice, the dual-control voltage-controlled oscillator 260 can be realized by adding a voltage control port and a varactor to a conventional VCO. By changing the resonant frequency of the resonant cavity, the DC level of the first control voltage controlling the phase- and self-injection-locked oscillator (the dual-control voltage-controlled oscillator 260) is adjusted to the original predetermined value, and there is no need to add any complicated control loops or radio-frequency circuit components. This effectively resolves the problem of saturation in the dynamic range of the conventional radar receiver (this problem is caused by DC offset), so that the detection of the microwave sensor is more stable and the detection failure due to change in external environment will not occur easily.

Figure 4A:
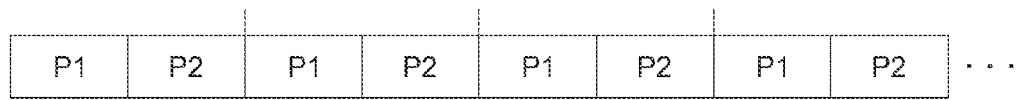
FIG. 4A and FIG. 4B respectively are a path switching control timing diagram according to an embodiment of the disclosure.
Figure 4B:
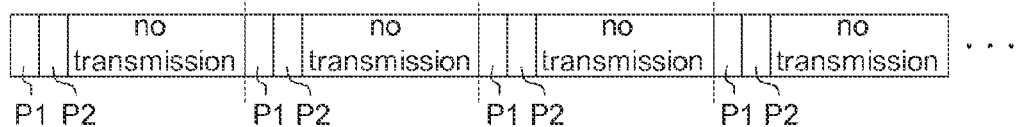

Referring to FIG. 4A and FIG. 4B, path switching control timing diagrams according to an embodiment of the disclosure are respectively shown. As indicated in FIG. 4A, by switching between the paths P1 and P2, transmission or reception of the sensing signals on the paths P1 and P2 is in different time slots, and the problem arising from sensing zero points in the paths could thus be avoided.

Besides, if the disturbance of the object under detection under detection is a low frequency signal (for example, the heart beat rate of human is about 72 beats/minute in the frequency of 1.2 Hz), then the transmission power can further be reduced in an embodiment of the disclosure. As indicated in FIG. 4B, exemplarily but not restrictively, the transmission time of the paths P1 and P2 is about 1 ms. If the non-transmission period (during which time no microwave signal is transmitted) is 48 ms, then the average frequency is 20 Hz, which is far higher than the frequency of the disturbance of the object under detection. In an embodiment of the disclosure, the transmission paths can be turned-off at non-sampling time periods of the two paths to reduce the average transmission power and almost without deteriorating the detection sensitivity. The switching timing of FIG. 4A and FIG. 4B can be controlled by a path switching controller (FIG. 2). The path switching controller transmits multiple switch control signals to control the multiple switches in the delay path switching unit.

Figure 5A:
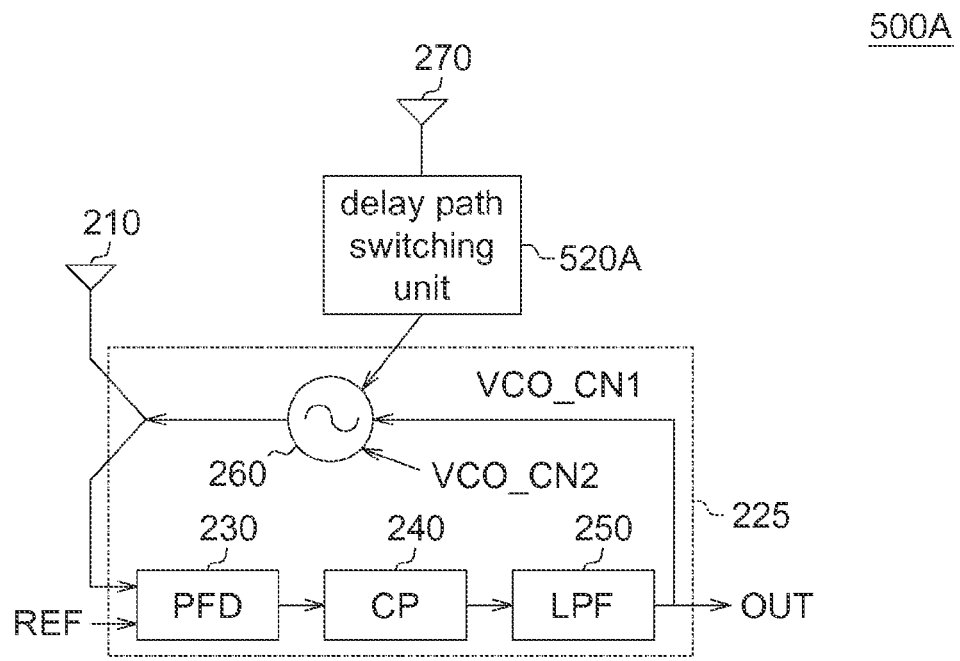
FIG. 5A and FIG. 5B respectively are a functional block diagram of a microwave motion sensor according to other embodiments of the disclosure.
Figure 5B:
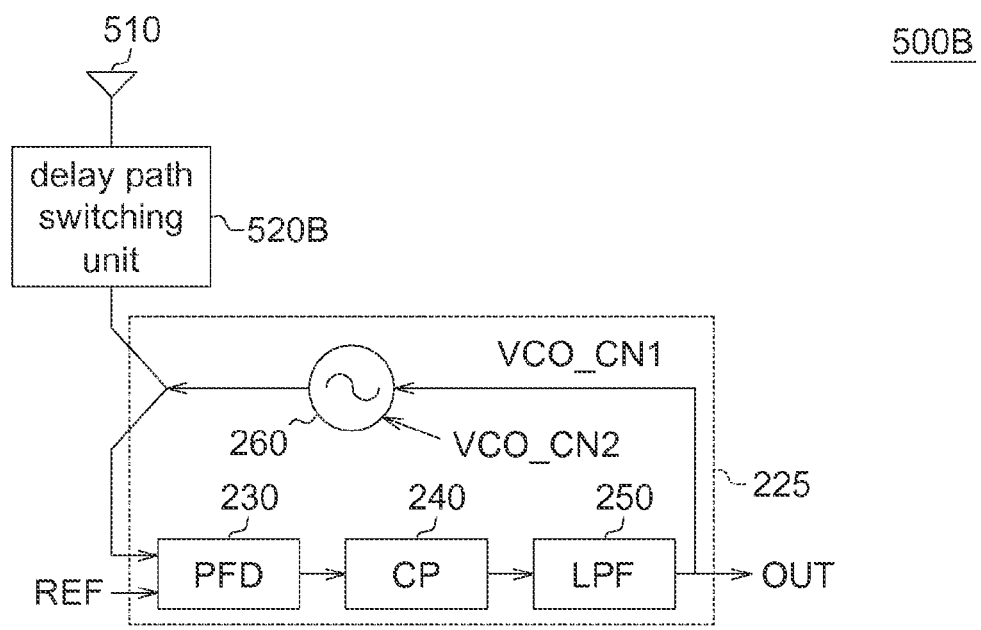

FIG. 5A and FIG. 5B respectively are functional block diagrams of a microwave motion sensor according to other embodiments of the disclosure. The comparison between FIG. 5A and FIG. 2 shows that in the microwave motion sensor 500A of FIG. 5A, the delay path switching unit 520A is used for switching between different transceiving paths. The comparison between FIG. 5B and FIG. 2 shows that in the microwave motion sensor 500B of FIG. 5B, an antenna 510 is capable of receiving and transmitting microwave signals. The delay path switching unit 520B of FIG. 5B is different from the delay path switching unit 220 of FIG. 2 is that the path phase shift is 45 degrees for example.

Besides, anyone who is skilled in the technology of the present disclosure will understand that any combinations of the above embodiments are still within the spirit of the present disclosure. For example, in other possible embodiments of the present disclosure, delay path switching units may be disposed in both the transmission paths and the reception paths for switching the transmission paths and the reception paths respectively. Details of the disposition of the delay path switching units are obtained from the above disclosure and the similarities are not repeated here.

The embodiments of the disclosure may be used for detecting such as but not limited to breaths, heartbeat, disturbance and vibration (such as the vibration of windows).

In the embodiments of the disclosure, path delay switching is with a self-injection-locked Doppler radar. However, in other embodiment of the disclosure, the path delay switching may also be with other architecture of single-frequency Doppler radar.

As disclosed in the above embodiments, the disclosure at least has many advantages exemplified below:

In an embodiment of the disclosure, to resolve the problem arising from sensing zero points (that is, external disturbances cannot be sensed in some positions), the transmission/reception paths with different phase shifts are switched, such that the sensing zero points in the transmission/reception paths do not overlap (the sensing zero points in the transmission/reception paths are even interlaced). By doing so, object are has under excellent sensing sensitivity in every position and the phenomenon of sensing zero points is eliminated. That is, the sensing sensitivities of these transmission/reception paths are complementary to each other.

In an embodiment of the disclosure, in detection low frequency motion/disturbance signal, a lower sampling frequency would suffice to detect the low frequency motion/ disturbance signal. Furthermore, there is no need to transmit electromagnetic wave at non-sampling time, so that the average transmission power is effectively reduced, and the concern of microwave exposure to human body can thus be relieved.

In an embodiment of the disclosure, a dual-control voltage-controlled oscillator is utilized to adjust the DC level to eliminate the DC offset, and there is no need to add any complicated control loops or radio frequency circuit components. The detection result of the microwave sensor is even more stable, and the detection failure due to change in external environment will not occur easily.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A microwave motion sensor, comprising:
 a transmitting device transmitting a microwave signal to a space under detection;
 a receiving device receiving a reflected microwave signal reflected from the space under detection;
 a signal processing device processing the reflected microwave signal received by the receiving device to judge whether there is a disturbance in the space under detection, wherein the signal processing device generates the microwave signal; and
 a delay path switching device coupled to the signal processing device and the transmitting device, wherein the delay path switching device switches a plurality of transmission paths having different delays and results in different phase shifts to the transmission paths which the microwave signal passes through,
 wherein,
 the signal processing device at least comprises a dual-control voltage-controlled oscillator, which generates the microwave signal;
 the signal processing device compares the microwave signal with a reference signal to obtain a first control voltage, which reflects an external disturbance information of the space under detection;
 an oscillation frequency of the dual-control voltage-controlled oscillator is determined by the first control voltage and a second control voltage; and
 wherein, in response to the dual-control voltage-controlled oscillator being affected by the external disturbance information and results in a DC offset to the first control voltage, the signal processing device generates a second voltage variation of the second control voltage according to a first voltage variation of the first control voltage to eliminate the DC offset of the first control voltage by the dual-control voltage-controlled oscillator.

2. The microwave motion sensor according to claim 1, wherein, a plurality of sensing zero points in these transmission paths are not overlapped with each other.

3. The microwave motion sensor according to claim 1, further comprising a delay path switching controller coupled to the delay path switching device to select one of these transmission paths.

4. The microwave motion sensor according to claim 3, wherein, the delay path switching controller turns off these transmission paths having different delays at non-sampling time periods.

5. The microwave motion sensor according to claim 1, wherein, the delay path switching device includes a delay unit, and at least two switches.

6. A microwave motion sensor, comprising:
 a transmitting device transmitting a microwave signal to a space under detection;
 a receiving device receiving a reflected microwave signal reflected from the space under detection;
 a delay path switching device coupled to the receiving device, wherein the delay path switching device switches a plurality of reception paths having different delays and results in different phase shifts to the reception paths which the reflected microwave signal passes through; and
 a signal processing device processing the reflected microwave signal received by the receiving device to judge whether there is a disturbance in the space under detection, wherein the signal processing device generates the microwave signal,
 wherein,
 the signal processing device at least comprises a dual-control voltage-controlled oscillator, which generates the microwave signal;
 the signal processing device compares the microwave signal with a reference signal to obtain a first control voltage, which reflects an external disturbance information of the space under detection;
 an oscillation frequency of the dual-control voltage-controlled oscillator is determined by the first control voltage and a second control voltage; and
 wherein, in response to the dual-control voltage-controlled oscillator being affected by the external disturbance information and results in a DC offset to the first control voltage, the signal processing device generates a second voltage variation of the second control voltage according to a first voltage variation of the first control voltage to eliminate the DC offset of the first control voltage by the dual-control voltage-controlled oscillator.

7. The microwave motion sensor according to claim 6, wherein, a plurality of sensing zero points in these reception paths are not overlapped with each other.

8. The microwave motion sensor according to claim 6, further comprising a delay path switching controller coupled to the delay path switching device to select one of these reception paths.

9. The microwave motion sensor according to claim 6, wherein, the delay path switching device includes a delay unit, and at least two switches.

10. A microwave motion sensor, comprising:
 a transceiving device, transmitting a microwave signal to a space under detection and receiving a reflected microwave signal reflected from the space under detection;
 a signal processing device processing the reflected microwave signal received by the transceiving device to judge whether there is a disturbance in the space under detection, wherein the signal processing device generates the microwave signal; and
 a delay path switching device coupled to the signal processing device and the transceiving device, wherein the delay path switching device switches a plurality of paths having different delays and results in different phase shifts to the paths which the microwave signal and the reflected microwave signal pass through,
 wherein,
 the signal processing device at least comprises a dual-control voltage-controlled oscillator, which generates the microwave signal;
 the signal processing device compares the microwave signal with a reference signal to obtain a first control voltage, which reflects an external disturbance information of the space under detection;

an oscillation frequency of the dual-control voltage-controlled oscillator is determined by the first control voltage and a second control voltage; and wherein, in response to the dual-control voltage-controlled oscillator being affected by the external disturbance information and results in a DC offset to the first control voltage, the signal processing device generates a second voltage variation of the second control voltage according to a first voltage variation of the first control voltage to eliminate the DC offset of the first control voltage by the dual-control voltage-controlled oscillator.

11. The microwave motion sensor according to claim 10, wherein, a plurality of sensing zero points in these paths are not overlapped with each other.

12. The microwave motion sensor according to claim 10, further comprising a delay path switching controller coupled to the delay path switching device to select one of these paths.

13. The microwave motion sensor according to claim 12, wherein, the delay path switching controller turns off these paths having different delays at non-sampling time periods.

14. The microwave motion sensor according to claim 10, wherein, the delay path switching device includes a delay unit, and at least two switches.

* * * * *